United States Patent [19]

Younkin et al.

[11] Patent Number: 5,449,609
[45] Date of Patent: Sep. 12, 1995

[54] METHODS FOR SCREENING FOR NEUROTOXICITY USING A CLONAL HUMAN TERATOCARCINOMA CELL LINE

[75] Inventors: Donald P. Younkin; David Pleasure, both of Wynnewood, Pa.

[73] Assignee: Children's Hospital of Philadelphia, Philadelphia, Pa.

[21] Appl. No.: 189,199

[22] Filed: Jan. 31, 1994

[51] Int. Cl.$^6$ ............................................. G01N 33/567
[52] U.S. Cl. .................................. 435/7.21; 435/7.1; 435/7.2; 435/26; 435/29
[58] Field of Search ................... 435/7.21, 7.1, 7.2, 435/29, 26

[56] References Cited

U.S. PATENT DOCUMENTS 5,175,103 12/1992 Lee et al. ........................ 435/172.3

OTHER PUBLICATIONS

Younkin et al, "Inducible expression of neuronal glutamate receptor channels in the NTZ human cell line", Proc. Natl. Acad. Sci. USA, 90(6):2174–2178 (Mar. 15, 1993).

Greengard et al, "Enhancement of the Glutamate Response by cAMP-Dependent Protein Kinase in Hippocampal Neurons", Science, 253: 1135–1138 (6 Sep. 1991).

Hardy et al, "Expression of Non-NMDA Glutamate Receptor Channel Genes by Clonal Human Neurons", J. Neurochem., 63: 482–489 (Aug. 1994).

Andrews et al., "Pluripotent Embryonal Carcinoma Clones Derived from the Human Teratocarcinoma Cell Line Tera-2", Lab. Invest. 50: 147–162 (1984).

Andrews, "Retinoic Acid Induces Neuronal Differentiation of a Cloned Human Embryonal Carcinoma Cell Line in Vitro", Dev. Biol. 103: 285–293 (1984).

Ascher & Nowak, "Quisqualate- and Kainate-Activated Channels in Mouse Central Neurones in Culture", J. Physiol. (Lond). 399: 227–245 (1988).

Ascher et al., "N-Methyl-D-Aspartate-Activated Channels of Mouse Central Neurones in Magnesium-Free Solutions" J. Physiol. (Lond). 399: 207–226 (1988).

Boulter et al., "Molecular Cloning and Functional Expression of Glutamate Receptor Subunit Genes", Science 249: 1033–1037 (1990).

Choi, "Glutamate Neurotoxicity and Diseases: Review of the Nervous System", Neuron. 1: 623–634 (1988).

Choi et al., "Glutamate Neurotoxicity in Cortical Cell Culture" J. Neurosci. 7: 357–368 (1987).

Collingridge et al., "Excitatory Amino Acids in Synaptic Transmission in the Schaffer Collateral–Commissural Pathway of the Rat Hippocampus", J. Physiol. (Lond). 334: 33–46 (1983).

Collingridge and Singer, "Excitatory Amino Acid Receptors and Synaptic Plasticity", Trends. Pharmacol. Sci. 11: 290–296 (1990).

Cull-Candy & Usowicz, "Multiple-Conductance Channels Activated by Excitatory Amino Acids in Cerebellar Neurons", Nature 325: 525–528 (1987).

Forsythe and Westbrook, "Slow Excitatory Postsynaptic Currents Mediated by N-Methyl-D-Aspartate Receptors on Cultured Mouse Central Neurones", J. Physiol. (Lond). 396: 515–533 (1988).

Gustafsson et al., "Long-Term Potentiation in the Hippocampus Using Depolarizing Current Pulses as the Conditioning Stimulus to Single Volley Synaptic Potentials", J. Neurosci 7: 774–780 (1987).

Hestrin et al., "Analysis of Excitatory Synaptic Action in Pyramidal Cells Using Whole-Cell Recording From Rat Hippocampal Slices", J. Physiol. (Lond). 422: 203–225 (1990).

Hollmann et al., "Cloning by Functional Expression of a Member of the Glutamate Receptor Channel", Nature 342: 643–648 (1989).

(List continued on next page.)

Primary Examiner—Toni R. Scheiner
Assistant Examiner—Donna C. Wortman
Attorney, Agent, or Firm—Woodcock Washburn Kurtz Mackiewicz & Norris

[57] ABSTRACT

Methods for screening for excitotoxic effects of an agent on neurons of the central nervous system are provided by the present invention.

1 Claim, 6 Drawing Sheets

OTHER PUBLICATIONS

Johnson & Ascher, "Glycine Potentiates the NMDA Response in Cultured Mouse Brain Neurons", *Nature* 325: 529–531 (1987).

Keinanen et al., "A Family of AMPA-Selective Glutamate Receptors", *Science* 249: 556–560 (1990).

Kiskin et al., "Excitatory Amino Acid Receptors in Hippocampal Neurons: Kainate Fails to Desensitize Them", *Neurosci. Lett.* 63: 225–230 (1986).

Lerma et al., "mRNA from NCB-20 Cells Encodes the N-Methyl-D-Aspartate/phencyclidine Recptor: A Xenopus Ooctye Expression Study", *Proc. Natl. Acad. Sci. USA* 86: 1708–1711 (1989).

Lester et al., "Channel Kinetics Determine the Time Course of NMDA Receptor-Mediated Synaptic Currents", *Nature* 346: 565–567 (1990).

Mayer et al., "Voltage-Dependent Block by $MG^{2+}$ of NMDA Responses in Spinal Cord Neurones", *Nature* 309: 261–263 (1984).

Mayer et al., "Regulation of NMDA Receptor Desensitization in Mouse Hippocampal Neurons by Glycine", *Nature* 338: 425–427 (1989).

Meguro et al., "Functional Characterization of a Heteromeric NMDA Receptor Channel Expressed from Cloned cDNAs", *Nature* 357: 70–74 (1992).

Monyer et al., "Heteromeric NMDA Receptors: Molecular and Functional Distinction of Subtypes", *Science* 256:1217–1221 (1992).

Morimoto & Koshland, "Excitatory Amino Acid Uptake and N-Methyl-D-Aspartate-Mediated Secretion in a Neural Cell Line", *Proc. Natl. Acad. Sci. USA* 87 3518–3521 (1990).

Moriyoshi et al., "Molecular Cloning and Characterization of the Rat NMDA Receptor", *Nature* 354: 31–37 (1991).

Murphy et al., "Glutamate Cytotoxicity in a Neuronal Cell Line is Blocked by Membrane Depolarization", *Br. Res.* 460: 155–160 (1988).

Murphy et al., "Calcium-Dependent Glutamate Cytotoxicity in a Neuronal Cell Line", *Neuron.* 2: 1547–1558 (1989).

Murphy et al., "Glutamate Toxicity in the Neuronal Cell Line Involves Inhibition of Cystine Transport Leading to Oxidative Stress", *Br. Res.* 444: 325–332 (1988).

Nowak et al., "Magnesium Gates Glutamate-Activated Channels in Mouse Central Neurones", *Nature* 307: 462–465 (1984).

Olney, "Inciting Excitototix Cytocide Among Central Neurons", *Adv. Exp. Med. Biol.* 203: 631–645 (1986).

Patneau & Mayer, "Structure-Activity Relationships for Amino Acid Transmitter Candidates Acting at N-Methyl-D-Aspartate and Quisqualate Receptors", *J. Neurosci.* 10: 2385–2399 (1990).

Pleasure et al., "Pure, Postmitotic, Polarized Human Neurons Derived from NTera 2 Cells Provide a System for Expressing Exogenous Proteins in Terminally Differentiated Neurons", *J. Neurosci.* 12: 1802–1815 (1992).

Ronnett et al., "Human Cortical Neuronal Cell Line: Establishment from a Patient with Unilateral Megalencephaly", *Science* 248, 603–605 (1990).

Rothman, "Synaptic Release of Excitatory Amino Acid Neurotransmitter Mediates Anoxic Neuronal Death", *J. Neurosci.* 4: 1884–1891 (1984).

Sather et al., "Glycine-Insensitive Desensitization of NMDA Responses in Cultured Mouse Embryonic Neurons", *Neuron.* 4: 725–731 (1990).

Sommer et al., "Flip and Flop: A Cell-Specific Functional Switch in Glutamate-Operated Channels of the CNS", *Science* 249: 1580–1585 (1990).

Sugihara et al., "Structures and Properties of Seven Isoforms of the NMDA Receptor Generated by Alternative Splicing", *Biochem. Biophys. Res. Com.* 185: 826–832 (1992).

Trussel & Fischbach, "Glutamate Receptor Desensitization and Its Role in Synaptic Transmission", *Neuron.* 3: 209–218 (1989).

```
NT2-N    GTGGGCATCTACANTGGNACCCACGTCATCCCTAATGACAGGAAGATCATCTGGCCAGGCGGAGAGACAG
         |||||||||||||| ||  |||||| ||||||||||||||||||||||||||||||||||||||||||||
rat      GTGGGCATCTACAATGGTACCCATGTCATCATCCCAAATGACAGGAAGATCATCTGGCCAGGAGAGACAG
             1090      1100      1110      1120      1130      1140      1150

AGAAGTCTCGAGGGTACCAGATGTCCACCAGAGTCGAAGATTGTGACGATCCACCAGGAGCCCTTCGTGTACGTCAAGC
         ||||||| ||||||||||||||| ||||||||  ||||| |||||||||| |||||||||||||||||||||||||||
rat      AGAAACCTCGAGGATACCAGATGTCCACCAGACTAAAGATAGTGACGATCCGCCAGGAGCCCTTCGTGTACGTCAAGC
             1160      1170      1180      1190      1200      1210      1220      1230

CCACGCTGAGTGATGGGACATGCAAGGAGAGTTCACAGTCAACGGCGACCCAGTCAAGAAGGTGATCTGCACCGGGC
         ||||| ||||||||||||||||||||||||||||||||||| |||||||||||||||||||||||||||| |||||
rat      CCACAATGAGTGATGGGACATGCAAAGAGAGTTCACAGTCAATGGTGACCCAGTCAAGAAGGTGATCTGTACGGGGC
             1240      1250      1260      1270      1280      1290      1300      1310

CCAACGACACGTCGCCGGGCAGCCCCCGCCACACGGTGCCTCAGTGTTGCTACGGCTTTTGCATAGACCTGCTCATCG
         |||| |||||||| |||||||||||| |||| ||||||||||||||||||||| ||||||||||||||||||||||
rat      CCAATGACACGTCCCCGGGCAGCCCCAGGCATACGGTGCCTCAGTGTTGCTATGGCTTCTGCATAGACCTGCTCATCA
             1320      1330      1340      1350      1360      1370      1380      1390

CTAATGACAGGAAGATCATCA
```

FIG. 3B

```
NT2-N    VGIYXGTHVIPNDRKIIWPGGET
         |||| |||||||||||||||||||
rat      VGIYNGTHVIPNDRKIIWPGGET
             370       380

EKSRGYQMSTRLKIVTIHQEPFVYVK
         || ||||||||||||||||||||||
rat      EKPRGYQMSTRLKIVTIHQEPFVYVK
             390       400       410

PTLSDGTCKEEFTVNGDPVKKVICTG
         || |||||||||||||||||||| ||
rat      PTMSDGTCKEEFTVNGDPVKKVICTG
             420       430

PNDTSPGSPRHTVPQCCYGFCIDLLI
         ||||||||| ||||||||| ||||||
rat      PNDTSPGSPRHTVPQCCYGFCIDLLI
             440       450       460
```

FIG.4A

+Mg²⁺
−Glycine

+ CNQX

FIG.4B

+ APV 40 pA
200 ms

METHODS FOR SCREENING FOR NEUROTOXICITY USING A CLONAL HUMAN TERATOCARCINOMA CELL LINE

GOVERNMENT SUPPORT

This invention was funded, at least in part by National Institutes of Health Grant NS08075 (D.P.), NS25044 (D.P.), and NS28158 (C.-M.T.). The U.S. government may have certain rights in the invention.

BACKGROUND OF THE INVENTION

Glutamate is the major excitatory neurotransmitter in the vertebrate central nervous system (CNS); Forsythe and Westbrook, *J. Physiol. (Lond).* 396:515-533 (1988) and Hestrin, et al., *J. Physiol.* (Lond). 422:203-225 (1990); and plays an important role in CNS plasticity and learning. Collingridge, et al., *J. Physiol.* (Lond). 334:33-46 (1983); Collingridge and Singer, Trends. *Pharmacol. Sci.* 11:290-296 (1990); and Gustafsson, et al., *J. Neurosci.* 7:774-780 (1987). Recently, three classes of neuronal glutamate receptors have been cloned, sequenced, and reconstituted in expression vectors. Moriyoshi, et al., *Nature* 354:31-37 (1991); Monyer, et al., *Science* 256: 1217-1221 (1992); Sugihara, et al., Biochem. *Biophys. Res. Corn.* 185:826-832 (1992); Megufo, et al., *Nature* 357:70-74 (1992); Boulter, et al., *Science* 249: 1033-1037 (1990); Keinanen, et al., *Science* 249: 556-560 (1990); and Sommer, et al., Science 249:1580-1585 (1990). One class, metabotropic glutamate receptors, transduce signals to the cell interior by a G-protein coupled mechanism. The other two classes, N-methyl-D-aspartate (NMDA) receptors and non-NMDA, or α-amino-3-hydroxy-5-methyl-4-isoxazole-propionate (AMPA)/kainate, receptors, are transplasma membrane channels permeable to $Na^+$, $K^+$, and $Ca^{++}$. Entry of excessive $Ca^{++}$ into the cell via intense activation of NMDA receptors, as occurs during brain ischemia, activates mechanisms which cause neuronal death. Rothman, *J. Neurosci.* 4:1884-1891 (1984); Olney, *Adv. Exp. Med. Biol.* 203:631-645 (1986); Choi, et al., *J. Neurosci.* 7:357-368 (1987); and Choi, *Neuron.* 1:623-634 (1988).

Prior studies of the physiological properties of NMDA receptors, and of glutamate excitotoxicity, depended largely upon the use of primary cultures of neurons prepared from immature rodent. Rothman, *J. Neurosci.* 4:1884-1891 (1984); Olney, *Adv. Exp. Med. Biol.* 203:631-645 (1986); Choi, et al., *J. Neurosci.* 7:357-368 (1987); Choi, *Neuron.* 1:623-634 (1988); Nowak, et al., *Nature* 307:462-465 (1984); Mayer, et al., *Nature* 309:261-263 (1984); Johnson & Ascher, *Nature* 325:529-531 (1987); and Patneau & Mayer, *J. Neurosci.* 10:2385-2399 (1990). Many neuron-like cell lines have been screened for glutamate receptor channels but glutamate receptor channels have not been reported. For example, glutamate excitotoxicity has been demonstrated in the neuroblastoma-embryonic retinal hybrid cell line, N18-RE-105, but this is not mediated via NMDA receptor-channels. Murphy, et al., *Br. Res.* 444:325-332 (1988); Murphy, et al., *Br. Res.* 460:155-160 (1988); and Murphy, et al., *Neuron.* 2:1547-1558 (1989). The HCN-1A cell line, established from human cerebral cortical neurons, stains positively for glutamate, but glutamate receptor channels have not been reported in HCN-1A cells. Ronnett, et al., *Science* 248, 603-605 (1990). Other neuronal cell lines, such as HT-4, demonstrate NMDA-sensitive neurotransmitter release; Morimoto & Koshland, *Proc. Natl. Acad. Sci. USA* 87:3518-3521 (1990); and NCB-20, a mouse neuroblastoma-Chinese hamster brain hybrid cell line, contain mRNA encoding the NMDA/phencyclidine receptor. Lerma, et al., *Proc. Natl. Acad. Sci. USA* 86:1708-1711 (1989). However, direct electrophysiological recordings, which are the signature of functional glutamate receptor channels, have not demonstrated NMDA receptor-channels in any neuronal cell line.

A cell line of human neurons suitable for pharmacological and molecular biological studies of neuronal glutamate receptor channels has not been available. Many neuronal cell lines have been screened for glutamate receptor channels, but direct electrophysiological recordings have not demonstrated NMDA receptor channels in any of these lines.

SUMMARY OF THE INVENTION

In accordance with the present invention are provided methods for screening for excitotoxic effects of an agent on neurons of the central nervous system comprising administering the agent to clonal neuronal cells which express glutamate receptor channels and measuring cellular response.

DETAILED DESCRIPTION OF THE INVENTION

The present invention provides a method of screening for neurotoxicity using human neuronal cell lines in which glutamate receptor (GluR) channels are expressed. Such human neuronal cell lines express both the NMDA and AMPA/kainate classes, after neuronal differentiation.

Glutamate receptor channels underlie a number of fundamental characteristics of the mammalian CNS, including nearly all excitatory transmission, synaptic plasticity, and endotoxin-mediated neuronal death.

NT2 cells are histologically undifferentiated, but have neurofilaments and other immunohistological features of primitive neuroblasts. Andrews et al., *Lab. Invest.*, 1984, 50, 147, demonstrated that retinoic acid treatment induced a small proportion of NT2 cells to express neurites and to generate action potentials. However at least 95% pure cultures of postmitotic, cholinergic neurons (NT2-N) cells have recently been produced. These cells have extensive neurotic processes which can be identified as axons and dendrites on the basis of immunocytochemical, morphological and functional criteria. NT2-N cells can be maintained in this undifferentiated state for eight weeks or more.

Such cells can be used to evaluate the expression of glutamate receptor channels and glutamate neurotoxicity in human neuronal cells.

Figure 1A:
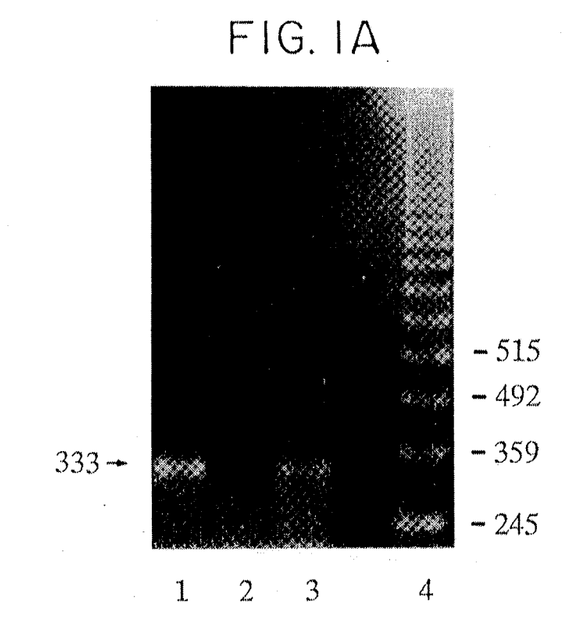
FIG. 1A is an ethidium bromide-stained agarose gel of PCR products. Lane 1 is PCR products from adult rat brain. Lane 2 PCR products from NT-2 cells. Lane 3 is PCR products from 2 week old NT2-N cells. Lane 4 is a nucleotide sizing ladder.
Figure 1B:
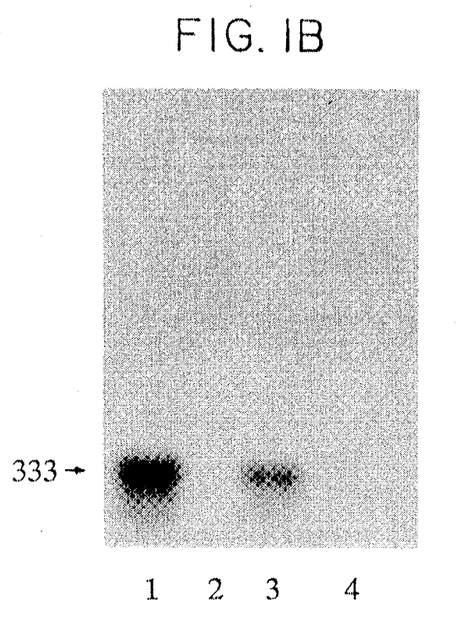
FIG. 1B is an autoradiogram of a Southern blot of PCR products. Lane 1 is PCR products from adult rat brain. Lane 2 PCR products from NT-2 cells. Lane 3 is PCR products from 2 week old NT2-N cells. Lane 4 is a nucleotide sizing ladder.
Figure 2:
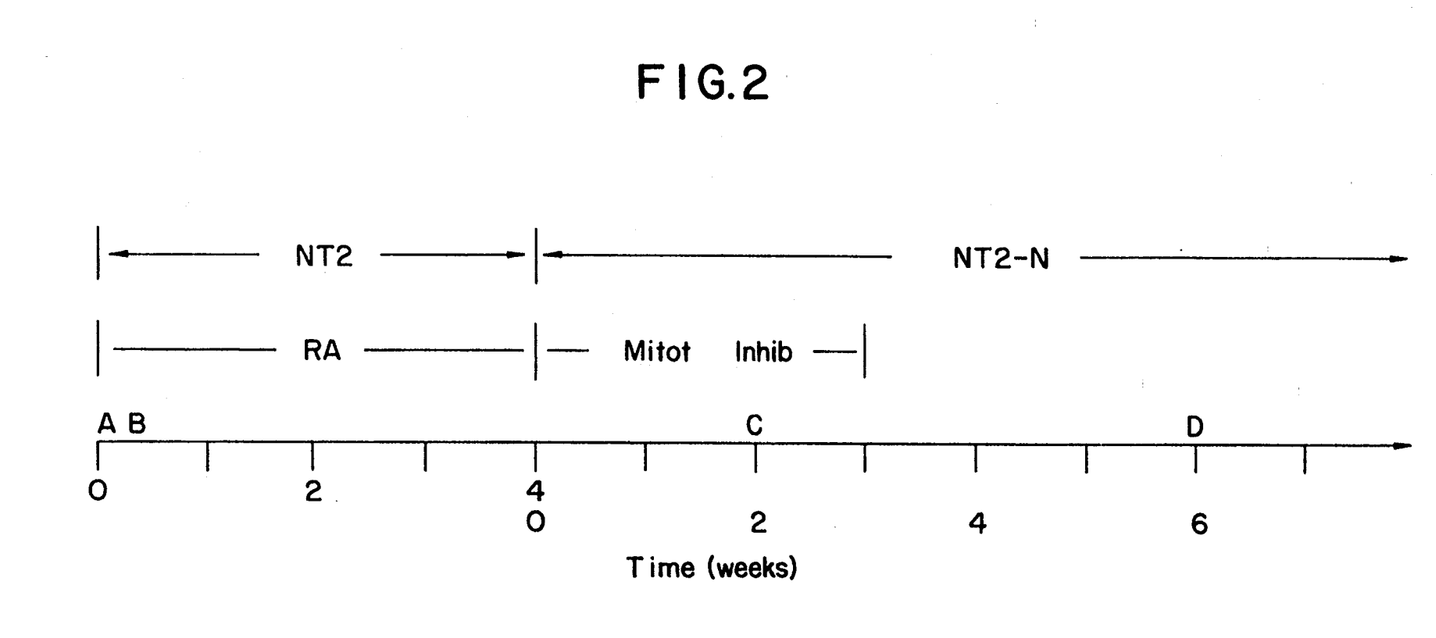
FIG. 2 is a time line illustrating the method used in treating and naming the cells and the ages (points A-D) at which the cells were studied.
Figure 3A:
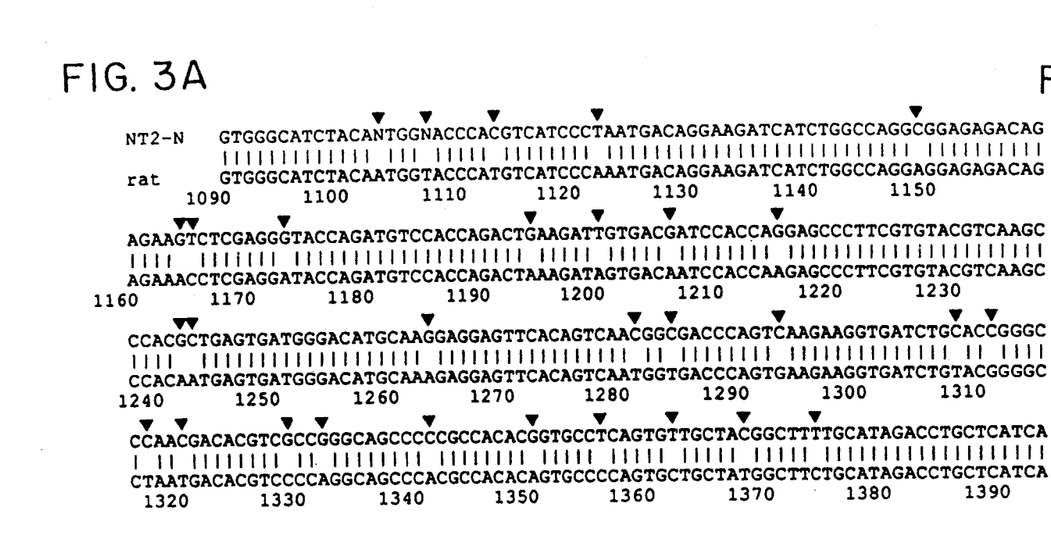
FIG. 3A is a comparison of the oligonucleotide sequence of the PCR amplified segment of the human NT2-N SEQ ID NO:1 and adult rat SEQ ID NO:2 NMDA receptor channel. Discrepancies between the rat and human sequences are indicated by arrowheads.
Figure 3B:
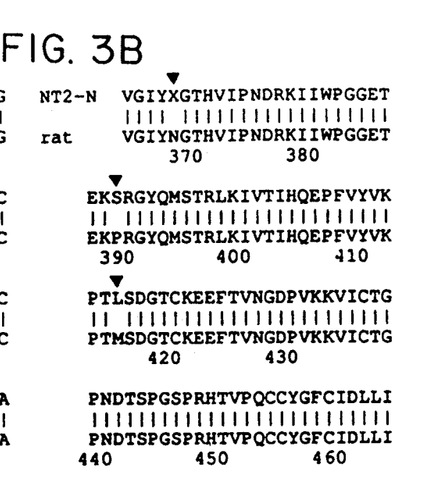
FIG. 3B is a comparison of the deduced amino acid sequence of the PCR amplified segment of the human NT2-N SEQ ID NO:3 and adult rat SEQ ID NO:4 NMDA receptor channel. Discrepancies between the rat and human sequences are indicated by arrowheads.

PCR amplification was used to establish that the NMDA receptor gene was expressed in NT2-N cells. PCR was used to amplify a 332 nucleotide sequence partially overlapping the putative glutamate binding domain of the rat NMDA receptor, NMDAR1. Moriyoshi, et al., *Nature* 354:31–37 (1991). FIGS. 1A and 1B illustrate that this amplification product was detected in 2 week old NT2-N cells (point C on timeline in FIG. 2), but not in untreated NT2 cells (point A in FIG. 2), or in NT2 cells that had been treated with retinoic acid for only 3 days (point B in FIG. 2, data not shown). The nucleotide sequence of the amplification product (FIG. 3A) was 90% homologous with the corresponding region of the rat NMDAR1 cDNA, and encodes an amino acid sequence 97% homologous with that of the corresponding domain of the rat NMDAR1 protein (FIG. 3B).

Figure 4A:
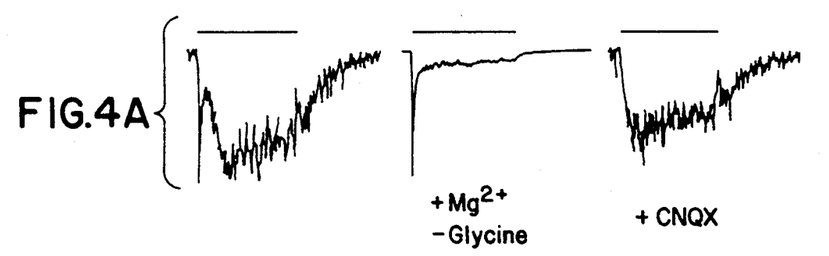
FIG. 4A shows cellular current under conditions which are permissive for current flow through NMDA and non-NMDA channels (left), selective for non-NMDA channels (center), or selective for NMDA channels (right).
Figure 4B:
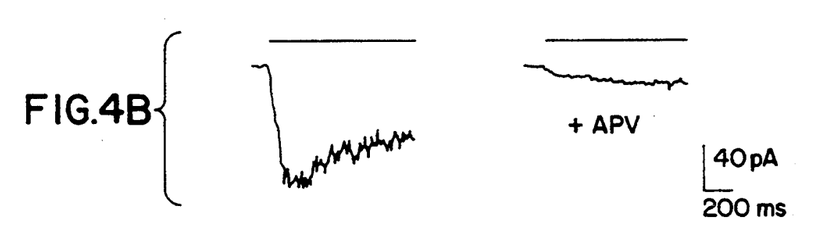
FIG. 4B shows cellular current in the presence (right) and absence (left) of antagonist DL-2-amino-5-phosphonovaleric acid.
Figure 4C:
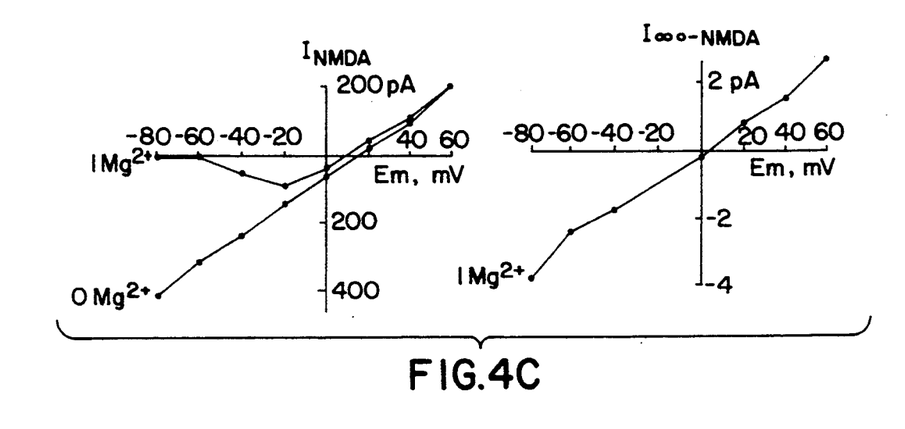
FIG. 4C shows the current-voltage (I-V) relationship for the NMDA-activated peak current with and without external $Mg^{+2}$ (left). The current-voltage (I-V) relationship for the fast transient glutamate-activated peak current is shown on the right.
Figure 5A:
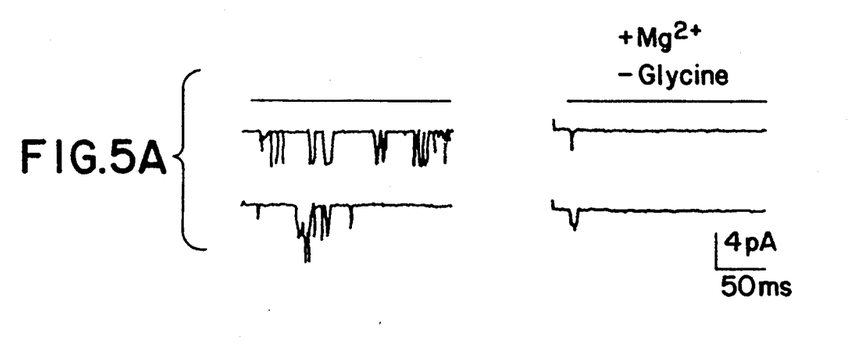
FIG. 5A shows the elimination of NMDA channel openings by the addition of external $Mg^{+2}$.
Figure 5B:
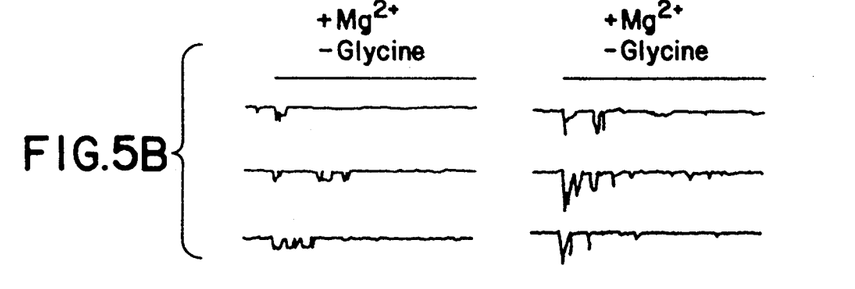
FIG. 5B shows a number of unitary conductances for the non-NMDA channels. Asterisks (*) identify openings with conductances <10 pS.
Figure 5C:
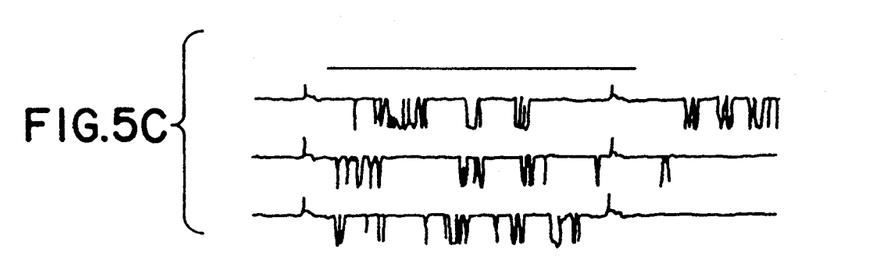
FIG. 5C shows high-conductance NMDA openings in the absence of external $Mg^{+2}$ and the presence of glycine (10μM) and 6-cyano-7-nitroquinoxaline-2,3-dione (CNQX) (5μM).
Figure 5D:
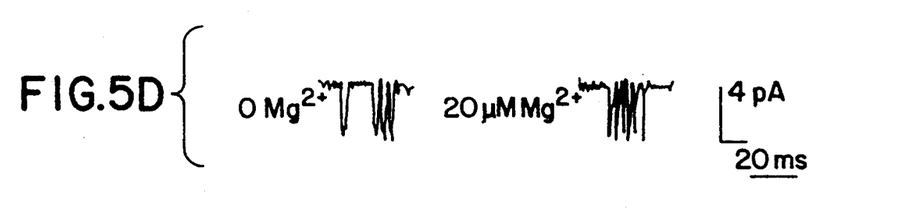
FIG. 5D shows flicker block of the NMDA openings by the presence of low concentrations of $Mg^+$.

Functional expression of glutamate receptor channels in NT2-N cells was examined using patch clamp techniques. Hamill, et al., *Pflugers Arch.* 391:85–100 (1981). Glutamate-evoked current became detectable in some NT2-N cells at 2 weeks (point C, FIG. 2), and were present in all cells by 6 weeks (point D, FIG. 2). FIG. 4A illustrates the whole cell currents from a 6 week old NT2-N cell evoked with rapid step applications of glutamate (500 μM) under conditions that were either permissive for current to flow through both the NMDA and non-NMDA channels (left trace), selective for non-NMDA channels (middle trace), or selective for NMDA channels (right trace). Two kinetically distinct current components were seen. There was an initial, rapidly activating, and desensitizing current which was selectively eliminated by addition of the non-NMDA antagonist, CNQX (5 μM; FIG. 4A). The initial current was followed by a second, slowly activating, desensitizing and deactivating current. Addition of $Mg^{++}$ and omission of glycine from the external perfusion solution selectively eliminated the slow current component. The latter two factors markedly attenuate current flow through NMDA channels. Nowak, et al., *Nature* 307:462–465 (1984); Mayer, et al., *Nature* 309:261–263 (1984); and Johnson & Ascher, *Nature* 325:529–531 (1987). FIG. 4B shows that the slowly activating and desensitizing current is activated by the step application of the selective agonist, NMDA (100 μM), and is attenuated by DL-2-amino-5-phosphonovaleric acid (APV) (200 μM). Further evidence that the slow current is mediated by NMDA channels is its voltage dependent block by external $Mg^{++}$. In the current-voltage (IV) relationship shown on the left of FIG. 4C, negligible amount of current is measured at membrane potential held below −40 mV in the presence of 1 mM $Mg^{++}$. In the absence of external $Mg^{++}$, the IV relationship is approximately linear. Reversal potential ranges between 10–15 mV under these recording conditions. On the other hand, the fast transient current remains approximately linear in the presence of external $Mg^{++}$ and reversal potential ranges between 0–5 mV. The $EC_{50}$ for the NMDA current component with glutamate as the agonist was 3.8 μM (n=7), which is close to that measured for the NMDA receptor in mouse hippocampal neurons. Patheau & Mayer, *J. Neurosci.* 10:2385–2399 (1990). The $EC_{50}$ for the peak and plateau components of the non-NMDA current were 270 and 15μM (n=12), respectively, results similar to those described in rat hippocampal neurons. Patneau & Mayer, *J. Neurosci.* 10:2385–2399 (1990); Kiskin, et al., *Neurosci. Lett.* 63:225–230 (1986); and Trussell & Fischbach, *Neuron.* 3:209–218 (1989).

Identification of multiple glutamate receptor channels in NT2-N cells at the single channel level is illustrated in FIG. 5. In primary neuronal cultures, NMDA channel openings are characterized by high unitary conductance (50 pS) and slow activation, desensitization, and deactivation kinetics. Ascher, et al., *J. physiol.* (Lond). 399:207–226 (1988); Mayer, et al., *Nature* 338:425–427 (1989); Sather, et al., *Neuron.* 4:725–731 (1990); and Lester, et al., *Nature* 346: 565–567 (1990). Non-NMDA channel openings are characterized by a number of different but generally lower unitary conductances; Tang, et al., *Science* 243:1474–1477 (1989); Cull-Candy & Usowicz, *Nature* 325:525–528 (1987); and Ascher & Nowak, *J. Physiol.* (Lond). 399:227–245 (1988); that open rapidly, then desensitize rapidly. FIG. 5A shows NMDA and non-NMDA channels coexisting in an excised NT2-N membrane patch. After the additional of $Mg^{++}$ and the elimination of glycine, only the non-NMDA channels remain. A 35 pS non-NMDA channel is illustrated in FIG. 5A. Lower conductance non-NMDA channels are recorded in two other patches shown in FIG. 5B. The existence of multiple subtypes of non-NMDA channels in NT2-N cells is consistent with and supports the concept of a heterogeneous family of non-NMDA glutamate receptor channels. Keinanen, et al., *Science* 249:556–560 (1990) and Hollmann, et al., *Nature* 342:643–648 (1989). FIG. 5C illustrates that NMDA channels in NT2-N cells have the characteristic high single channel conductance and slow gating kinetics described for CNS neurons. One subtle difference is the relatively slower activation of NT2-N channels. FIG. 5D illustrates rapid "flickery" block of the NT2-N NMDA channels by low concentration of $Mg^{++}$. These data clearly show that the NT2-N cells express glutamate receptor channels similar to those found in acutely dissociated and primary cultured mammalian neurons.

Figure 6A:
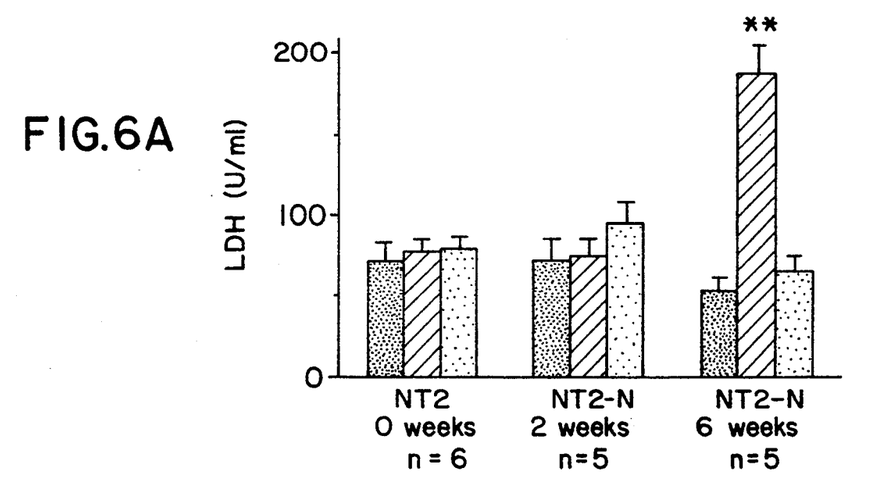
FIG. 6A is a schematic representation of glutamate cytotoxicity in NT2 and NT2-N cells at 0, 2, and 6 weeks measured by lactate dehydrogenase (LDH) release. ■: control. ▫: glutamate. ▫: glutamate plus MK801.
Figure 6B:
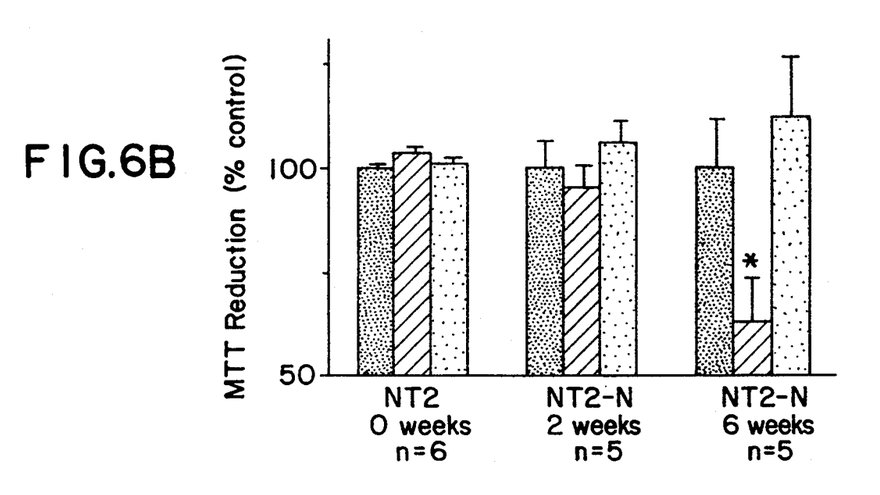
FIG. 6B is a schematic representation of glutamate cytotoxicity in NT2 and NT2-N cells at 0, 2, and 6 weeks measured by 3-(4,5-dimethylthiazol-2-yl)-2,5-diphenyltetrazolium bromide (MTT) reduction. ■: control. ▫: glutamate. ▫: glutamate plus MK801.

To determine if NT2-N cells are susceptible to glutamate excitotoxicity, cultures were exposed to glutamate, then examined for loss of plasma membrane integrity and mitochondrial function. Exposure to 1 mM L-glutamate for 15 minutes (FIG. 6) in a medium containing L-glycine and devoid of $Mg^{++}$ reproducibly damaged NT2-N cells when they were 6 weeks old. NT2 cells and 2 week old NT2-N cells were not injured. This time feature parallels the development of neuritic polarity in NT2-N cells. Pleasure, et al., *J. Neurosci.* 12:1802–1815 (1992). Glutamate cytotoxicity was blocked by MK-801. Thus, the appearance of glutamate excitotoxicity accompanies the appearance of neuritic polarity, a characteristic of terminally differentiated neurons.

The ability to induce glutamate receptor channel expression in the NT2 human cell line is significant for several reasons. First, it provides an opportunity to study regulation of NMDA and AMPA/kainate glutamate receptor gene expression in a model system that is both clonal and neuronal. Second, because this line is amenable to molecular biological manipulations such as stable transfection and subcloning; Pleasure, et al., *J. Neurosci.* 12:1802–1815 (1992); it should be possible to manipulate the specific subunit composition of the various glutamate receptor channels, thus permitting correlation of molecular structure and physiologic properties. Third, because of their human origin and because prior to exposure to retinoic acid these cells are capable of rapid proliferation, the NT2 cell line will provide an unlimited supply of a homogenous population of cells for the study of glutamate receptor channels in relation to human neurological disorders.

Thus, in accordance with methods of the present invention excitotoxic effects of an agent may be observed by measuring cellular response of cells expressing glutamate receptor channels. For example, lactate dehydrogenase (LDH) levels or mitochondrial levels may be observed. Reduced LDH or mitochondrial levels are indicative of excitotoxic effects. Cell death may also be indicative of excitotoxic effects.

The following examples are illustrative and are not meant to be limiting of the present invention.

EXAMPLES

Example 1

CELL CULTURE

NT2 cells were grown in OptiMEM-I (Gibco) supplemented with 5% (volume/volume) fetal bovine serum (FBS) and penicillin/streptomycin (P/S) as previously described. Andrews, *Dev. Biol.* 103:285–293 (1984); Andrews, et al., *Lab. Invest.* 50:147–162 (1984) and Pleasure, et al., *J. Neurosci.* 12:1802–1815 (1992).

For differentiation, NT2 cells were treated with $10^{-6}M$ retinoic acid (RA) twice weekly for four weeks. The cells were then replated in Dulbecco's modified Eagles's medium high glucose (DMEM/ HG) with 10% FBS and P/S. One day later, the NT2-N cells were mechanically dislodged and replated on Matri gel (Collaborative Research) coated dishes. For the next 2-3 weeks, the NT2-N cells were maintained in either DMEM/ HG supplemented with 10% FBS, P/S, cytosine arabinoside (1 μM), fluorodeoxyuridine (10 μM), and uridine (10 μM), or OptiMEM-I supplemented with 5% FBS, P/S and the same mitotic inhibitors. Thereafter, NT2-N cells were maintained in Opti-MEM-I supplemented with 5% FBS and P/S.

Example 2

PCR AND DNA SEQUENCING

Total RNA was isolated by the method of Chomczynski and Sacchi, *Anal. Biochem.* 162:156–159 (1987). The PCR amplification protocol was similar to that of Reddy and Pleasure, *J. Neurosci. Res.* 31:670–677 (1992). The PCR primers used were: 5' primer: 5'-AACCTGCAGAACCGCAAG-3' (SEQ ID NO:5) and 3' primer: 5'-GCTTGATGAGCAGGTCTATGC-3' (SEQ ID NO:6) Five μg of total RNA were used for reverse transcription in each case. The amplification profile involved denaturation at 94° C. for 1 minute, primer annealing at 45° C. for 1 minute, and extension at 72° C. for 1 minute. This cycle was repeated 30 times. The amplified DNA was ethanol-precipitated, and the pellet was dried, dissolved in TE buffer, and electrophoresed in a 2.5% agarose gel. An oligonucleotide, 5'-CACAGTCAATGGTGACCCAG-3' (SEQ ID NO:7) which spanned a portion of the region between the two primers in the reported sequence for the rat NMDAR1 cDNA; Moriyoshi, et al., *Nature* 354:31–37 (1991); was kinase labeled and used as a probe for Southern blotting. Sambrook, et al., *Molecular cloning. A laboratory manual* (Cold Spring Laboratory Press, Cold Spring Harbor, N.Y.) (1989). Exposure of the autoradiogram was for 30 minutes.

PCR products were extracted from gel slices using GeneClean II (Midwest Scientific, Valley Park, Mo.). Approximately 300 ng of each isolated band was sequenced with 3.2 pmole of the 5' primer using a Taq DyeDeoxy Terminator Cycle Sequencing Kit (Applied Biosystems, Foster City, Calif.). The cycle sequencing reactions were performed in a Perkins-Elmer 9600 thermal cycler for 25 cycles with a profile of 96° C. for 15 seconds, 50° C. for 1 second and 60° C. for 4 minutes. Following separation of the extension products on a Select-D G-50 column (5 Prime-3 Prime, Inc. Boulder, Colo.), the reactions were dried, resuspended in 4 ml of 5:1 formamide/50 mM EDTA, loaded on a 6% sequencing gel and analyzed using an Applied Biosystems 373 fluorescent sequencer.

Example 3

EXCITOTOXICITY

To determine if NT2-N cells are susceptible to glutamate excitotoxicity, cultures were exposed to glutamate, then examined for loss of plasma membrane integrity (by assaying release of lactate dehydrogenase; Koh & Choi, *J. Neurosci. Meth.* 20:83–90 (1987)) and loss of mitochondrial function (by measuring their capacity to cleave 3-(4,5-dimethylthiazol-2-yl)-2,5-diphenyl tetrazolium bromide (MTT) to a formazan product; Mosmann, *J. Immunol. Meth.* 65:55–63 (1983)). Cells were studied at three time points. NT2 cells (point A, FIG. 2), were studied prior to RA treatment. NT2-N cells were studied 2 and 6 weeks after replating on Matrigel (points C and D, FIG. 2). Cells were washed once with Dulbecco's phosphate buffered saline (PBS, 37° C.), then exposed to the indicated media for 15 minutes at 37° C. Control cells were exposed to a control salt solution (CSS) containing NaCl 120 mM, KCl 5.4 mM, $CaCl_2$ 1.8 mM, glucose 15 mM, Hepes 25 mM, glycine 50 $\mu$M, pH 7.4. 1 mM L-glutamate was added to CSS in the presence or absence of 300 nM MK801. Following the exposure, cells were washed twice with PBS, then fed with OptiMEM-I without fetal bovine serum and returned to the incubator. LDH and MTT reduction were measured 24 hours later. Previous studies indicated that the cells could survive in Opti-MEM-I without FBS for longer than 48 hours without changing morphology, releasing LDH or decreasing MTT reduction. LDH was measured in the culture media by colorimetric detection of pyruvate; Cabaud & Wroblewski, *Am. J. Clin. Pathol.* 30:234–239 (1958); using a Sigma diagnostic kit (Sigma Kit 500) and the modification of Priestley et al. *Br. Res.* 531:183–188 (1990). MTT reduction was measured by the colorimetric detection of the formazan product of MTT (3-(4,5-dimethylthiazol-2-yl)-2,5-diphenyl tetrazolium bromide) cleaved in active mitochondria (Promega Cell Titer 96). The result was used as an estimate of the number of functioning mitochondria present in the culture dish, and indirectly the number of functionally intact cells; Mosmann, *J. Immunol. Meth.* 65:55–63 (1983). Values are reported as mean±SEM. There were no differences between treatment groups with NT2 and 2 week-old NT2-N cells. In 6 week old NT2-N cells, glutamate exposure caused increased LDH release (**, $P<0.001$ by ANOVA) and decreased MTT reduction (*, $P<0.05$, ANOVA).

Example 4

ELECTROPHYSIOLOGY

Membrane currents were measured under voltage-clamp condition in either whole-cell or outside-out configuration of the patch-clamp technique. Hamill, et al., *Pflugers Arch.* 391:85–100 (1981). Recordings of single-channel currents were first filtered at 2 kHz and then digitized at 5 kHz. Rapid step changes of external solutions were achieved in less than one msec as previously described. Tang, et al., *Science* 243:1474–1477 (1989). External solutions consisted of NaCl, 150 mM $CaCl_2$, 2 mM; KCl, 3 mM; HEPES, 10 mM, buffered to pH 7.3. No $Mg^{++}$ and 10 $\mu$M of glycine were present unless otherwise marked; 1 mM $MgCl_2$ and no glycine were present for recordings marked +$Mg^{2+}$-Glycine. The internal pipette solution consisted of $CsMeSO_4$, 140 mM; HEPES, 10 mM; NaBapta, 5 mM; $MgCl_2$, 1 mM; $CaCl_2$, 2 mM; buffered to p H 7.3. To establish the $EC_{50}$ for the glutamate evoked current responses, glutamate concentrations between 0.2 and 5,000 $\mu$M were used.

What is claimed is:

1. A method for screening for excitotoxic effects of an agent on neurons of the central nervous system comprising administering the agent to NT2-N clonal neuronal cells and measuring cellular response, wherein a change in cellular response in the presence of the agent as compared to cellular response in the absence of the agent represents a positive screening result for excitotoxic effects.

* * * * *

UNITED STATES PATENT AND TRADEMARK OFFICE
CERTIFICATE OF CORRECTION

PATENT NO. : 5,449,609
DATED : September 12, 1995
INVENTOR(S) : Younkin et al.

It is certified that error appears in the above-indentified patent and that said Letters Patent is hereby corrected as shown below:

At column 1, line 26 delete "Corn." and insert --- Com. --- therefor.

At column 1, line 26 delete "Megufo" and insert --- Meguro --- therefor.

At column 3, line 6 delete "Mg$^+$" and insert --- Mg$^{+2}$ --- therefor.

At column 4, line 39 delete "Patheau" and insert --- Patneau --- therefor.

At column 4, line 52 delete "J. physiol." and insert --- J. Physiol. --- therfor.

At column 6, line 6 delete "Matri gel" and insert --- Matrigel --- therefor.

Signed and Sealed this

Ninth Day of July, 1996

*Attest:*

BRUCE LEHMAN

*Attesting Officer*     Commissioner of Patents and Trademarks

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 302 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:1:

| | | | | | | |
|---|---|---|---|---|---|---|
| GTGGGCATCT | ACATGGACCC | ACGTCATCCC | TAATGACAGG | AAGATCATCT | GGCCAGGCGG | 60 |
| AGAGACAGAG | AAGTCTCGAG | GGTACCAGAT | GTCCACCAGA | CTGAAGATTG | TGACGATCCA | 120 |
| CCAGGAGCCC | TTCGTGTACG | TCAAGCCCAC | GCTGAGTGAT | GGGACATGCA | AGGAGGAGTT | 180 |
| CACAGTCAAC | GGCGACCCAG | TCAAGAAGGT | GATCTGCACC | GGGCCCAACG | ACACGTCGCC | 240 |
| GGGCAGCCCC | CGCCACACGG | TGCCTCAGTG | TTGCTACGGC | TTTTGCATAG | ACCTGCTCAT | 300 |
| CA | | | | | | 302 |

( 2 ) INFORMATION FOR SEQ ID NO:2:

( i ) SEQUENCE CHARACTERISTICS:
        ( A ) LENGTH: 304 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:2:

```
GTGGGCATCT ACAATGGTAC CCATGTCATC CCAAATGACA GGAAGATCAT CTGGCCAGGA        60

GGAGAGACAG AGAAACCTCG AGGATACCAG ATGTCCACCA GACTAAAGAT AGTGACAATC       120

CACCAAGAGC CCTTCGTGTA CGTCAAGCCC ACAATGAGTG ATGGGACATG CAAAGAGGAG       180

TTCACAGTCA ATGGTGACCC AGTGAAGAAG GTGATCTGTA CGGGGCCTAA TGACACGTCC       240

CCAGGCAGCC CACGCCACAC AGTGCCCCAG TGCTGCTATG GCTTCTGCAT AGACCTGCTC       300

ATCA                                                                    304
```

( 2 ) INFORMATION FOR SEQ ID NO:3:

( i ) SEQUENCE CHARACTERISTICS:
        ( A ) LENGTH: 100 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

```
Val Gly Ile Tyr Gly Thr His Val Ile Pro Asn Asp Arg Lys Ile Ile
 1               5                  10                  15

Trp Pro Gly Gly Glu Thr Glu Lys Ser Arg Gly Tyr Gln Met Ser Thr
            20                  25                  30

Arg Leu Lys Ile Val Thr Ile His Gln Glu Pro Phe Val Tyr Val Lys
        35                  40                  45

Pro Thr Leu Ser Asp Gly Thr Cys Lys Glu Glu Phe Thr Val Asn Gly
    50                  55                  60

Asp Pro Val Lys Lys Val Ile Cys Thr Gly Pro Asn Asp Thr Ser Pro
65                  70                  75                  80

Gly Ser Pro Arg His Thr Val Pro Gln Cys Cys Tyr Gly Phe Cys Ile
                85                  90                  95

Asp Leu Leu Ile
            100
```

( 2 ) INFORMATION FOR SEQ ID NO:4:

( i ) SEQUENCE CHARACTERISTICS:
        ( A ) LENGTH: 101 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:4:

```
Val Gly Ile Tyr Asn Gly Thr His Val Ile Pro Asn Asp Arg Lys Ile
 1               5                  10                  15

Ile Trp Pro Gly Gly Glu Thr Glu Lys Pro Arg Gly Tyr Gln Met Ser
            20                  25                  30

Thr Arg Leu Lys Ile Val Thr Ile His Gln Glu Pro Phe Val Tyr Val
        35                  40                  45

Lys Pro Thr Met Ser Asp Gly Thr Cys Lys Glu Glu Phe Thr Val Asn
    50                  55                  60

Gly Asp Pro Val Lys Lys Val Ile Cys Thr Gly Pro Asn Asp Thr Ser
65                  70                  75                  80

Pro Gly Ser Pro Arg His Thr Val Pro Gln Cys Cys Tyr Gly Phe Cys
                85                  90                  95

Ile Asp Leu Leu Ile
            100
```

( 2 ) INFORMATION FOR SEQ ID NO:5:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

AACCTGCAGA ACCGCAAG      18

( 2 ) INFORMATION FOR SEQ ID NO:6:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

GCTTGATGAG CAGGTCTATG C      21

( 2 ) INFORMATION FOR SEQ ID NO:7:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

CACAGTCAAT GGTGACCCAG      20